(12) United States Patent
Pearson

(10) Patent No.: US 11,484,641 B2
(45) Date of Patent: Nov. 1, 2022

(54) PATIENT TRANSPORT PLATFORM AND MOBILE MEDICAL EQUIPMENT CONNECTOR SMART DEVICE

(71) Applicant: Matthew Lee Pearson, Trussville, AL (US)

(72) Inventor: Matthew Lee Pearson, Trussville, AL (US)

(*) Notice: Subject to any disclaimer, the term of this patent is extended or adjusted under 35 U.S.C. 154(b) by 353 days.

(21) Appl. No.: 16/897,670

(22) Filed: Jun. 10, 2020

(65) Prior Publication Data

US 2020/0390969 A1    Dec. 17, 2020

Related U.S. Application Data

(60) Provisional application No. 62/860,466, filed on Jun. 12, 2019.

(51) Int. Cl.
*A61M 5/14* (2006.01)
*A61G 12/00* (2006.01)
*A61G 7/05* (2006.01)

(52) U.S. Cl.
CPC ......... *A61M 5/1415* (2013.01); *A61G 7/0503* (2013.01); *A61G 12/008* (2013.01); *A61G 2203/12* (2013.01); *A61G 2203/46* (2013.01); *A61G 2203/78* (2013.01); *A61G 2203/80* (2013.01); *A61M 2209/082* (2013.01)

(58) Field of Classification Search
CPC ............... A61G 7/0503; A61G 12/008; A61G 2203/12; A61G 2203/46; A61G 2203/78; A61G 2203/80; A61M 5/1415; A61M 5/1414; A47C 21/00; A47C 19/22; A47C 31/00

USPC ............... 5/658, 503.1, 600; 280/292, 288.4
See application file for complete search history.

(56) References Cited

U.S. PATENT DOCUMENTS

| | | | | |
|---|---|---|---|---|
| 3,709,372 A | * | 1/1973 | Alexander | A61M 5/1415 5/503.1 |
| 4,511,157 A | * | 4/1985 | Wilt, Jr. | A61M 5/1415 297/188.2 |
| 4,511,158 A | * | 4/1985 | Varga | A61G 7/05 248/229.11 |
| 4,572,536 A | * | 2/1986 | Doughty | A61G 7/05 297/188.2 |
| 4,600,209 A | * | 7/1986 | Kerr, Jr. | A61G 7/0503 5/503.1 |

(Continued)

FOREIGN PATENT DOCUMENTS

| | | | | |
|---|---|---|---|---|
| AU | 2005100583 A4 | * | 8/2005 | A61M 5/1415 |
| GB | 2428383 A | * | 1/2007 | A61G 12/008 |

(Continued)

*Primary Examiner* — Robert G Santos
(74) *Attorney, Agent, or Firm* — Wright Lindsey Jennings, LLP; Meredith Lowry

(57) ABSTRACT

A device for selectively connecting mobile medical equipment, such as an IV pole, to a patient transport platform such that the medical equipment and patient transport platform can move together, thus providing a patient mobility while maintaining the patient's connection to the mobile medical equipment and therefore eliminating the necessity to disconnect an existing medical equipment (such as IV pole) and transfer the patient to a new medical equipment, while also allowing monitoring of patient movement and activity via electronics in the device.

12 Claims, 16 Drawing Sheets

(56) References Cited

U.S. PATENT DOCUMENTS

| | | | | |
|---|---|---|---|---|
| 4,729,576 A * | 3/1988 | Roach | B60D 1/249 | 280/493 |
| 4,767,131 A * | 8/1988 | Springer | A61G 5/10 | 297/188.2 |
| 4,840,391 A * | 6/1989 | Schneider | A61M 5/1415 | 248/231.51 |
| 4,886,237 A * | 12/1989 | Dennis | A61G 7/05 | 248/316.5 |
| 4,969,768 A * | 11/1990 | Young | F16M 11/08 | 403/97 |
| 5,009,442 A * | 4/1991 | Schneider | C07D 233/64 | 248/231.41 |
| 5,118,127 A * | 6/1992 | Partington | A61G 7/05 | 280/483 |
| 5,149,036 A * | 9/1992 | Sheehan | F16L 3/02 | 248/304 |
| 5,219,139 A * | 6/1993 | Hertzler | A61G 5/10 | 248/276.1 |
| 5,236,213 A * | 8/1993 | Trickett | F16M 11/42 | 403/97 |
| 5,288,093 A * | 2/1994 | Gross | A61G 5/10 | 248/230.6 |
| 5,292,094 A * | 3/1994 | VanKuiken | A61G 5/10 | 248/125.1 |
| 5,355,539 A * | 10/1994 | Boettger | A61G 7/05 | 5/503.1 |
| 5,358,205 A * | 10/1994 | Starkey | F16B 7/0493 | 248/220.21 |
| 5,374,074 A * | 12/1994 | Smith | A61G 5/10 | D12/131 |
| 5,421,548 A * | 6/1995 | Bennett | A61G 12/008 | 5/503.1 |
| 5,509,680 A * | 4/1996 | Scharf | A61G 5/1054 | 248/282.1 |
| 5,588,166 A * | 12/1996 | Burnett | F16L 3/1075 | 5/503.1 |
| 5,699,988 A * | 12/1997 | Boettger | A61G 7/05 | 248/316.1 |
| 5,704,577 A * | 1/1998 | Gordon | F16B 7/0493 | 248/230.1 |
| 5,898,961 A * | 5/1999 | Ambach | A61G 7/05 | 292/108 |
| 6,073,285 A * | 6/2000 | Ambach | A61G 7/0513 | 5/503.1 |
| 6,079,678 A * | 6/2000 | Schott | A61M 5/1415 | 5/503.1 |
| 6,179,260 B1 * | 1/2001 | Ohanian | A61G 7/05 | 403/374.1 |
| 6,375,133 B1 * | 4/2002 | Morrow | A61M 5/1415 | 5/503.1 |
| 6,619,599 B2 * | 9/2003 | Elliott | A61M 5/1415 | 5/503.1 |
| 6,688,569 B1 * | 2/2004 | Weiss | B25B 5/10 | 403/321 |
| 7,258,310 B2 * | 8/2007 | Norris | A61G 5/10 | 248/125.7 |
| 7,637,464 B2 * | 12/2009 | Heimbrock | A61G 7/05 | 248/224.51 |
| 8,011,629 B2 * | 9/2011 | Herskovic | F16M 13/02 | 248/229.15 |
| 8,100,371 B2 * | 1/2012 | Eggleston | A61G 12/008 | 5/601 |
| 8,459,602 B2 * | 6/2013 | Herskovic | F16M 11/2035 | 248/229.15 |
| 10,786,407 B2 * | 9/2020 | Ellis | B60D 1/143 | |
| 11,007,102 B2 * | 5/2021 | Patmore | A61G 7/05 | |
| 11,229,735 B1 * | 1/2022 | Alves | F16M 11/041 | |
| 2002/0104934 A1 * | 8/2002 | Elliott | A61M 5/1415 | 248/407 |
| 2004/0075228 A1 * | 4/2004 | Duffey | A61G 7/05 | 280/47.38 |
| 2005/0150851 A1 * | 7/2005 | Norris | A61G 5/10 | 211/107 |
| 2007/0023587 A1 * | 2/2007 | Eggleston | A61M 5/1415 | 248/98 |
| 2007/0176063 A1 * | 8/2007 | Heimbrock | A61G 7/015 | 248/176.1 |
| 2007/0267556 A1 * | 11/2007 | Herskovic | F16M 11/06 | 248/218.4 |
| 2011/0121149 A1 * | 5/2011 | Herskovic | A61G 7/0503 | 248/223.41 |
| 2019/0060149 A1 * | 2/2019 | Patmore | A61G 7/1046 | |
| 2019/0380894 A1 * | 12/2019 | Ellis | B60D 1/52 | |
| 2020/0390969 A1 * | 12/2020 | Pearson | A61G 12/008 | |
| 2021/0146038 A1 * | 5/2021 | Johnson | B62B 3/025 | |

FOREIGN PATENT DOCUMENTS

| | | | | |
|---|---|---|---|---|
| WO | WO-2005056085 A1 * | 6/2005 | | A61G 12/008 |
| WO | WO-2008042346 A2 * | 4/2008 | | A61G 12/004 |
| WO | WO-2008098306 A1 * | 8/2008 | | A61G 7/0503 |
| WO | WO-2021101942 A1 * | 5/2021 | | A61M 5/1415 |

* cited by examiner

PATIENT TRANSPORT PLATFORM AND MOBILE MEDICAL EQUIPMENT CONNECTOR SMART DEVICE

CROSS REFERENCE TO RELATED APPLICATIONS

This application claims the benefit of U.S. Provisional Patent Application No. 62/860,466, filed on Jun. 12, 2019, and entitled "Patient Transport Platform and Mobile Medical Equipment Connector Smart Device." Such application is incorporated by reference herein in its entirety.

STATEMENT REGARDING FEDERALLY SPONSORED RESEARCH OR DEVELOPMENT

Not applicable.

BACKGROUND OF THE INVENTION

In hospitals, patients are typically transported around the hospital for various purposes including for moving from one treatment to another or just for a quick change of scenery. Many times, patients are hooked up to medical equipment or may have an IV and thus this equipment must also be transported with the patient. Traditionally the hospital gurneys, wheelchairs, and wagons (in the case of pediatric hospitals) are used to transport the patients. These patient transport platforms are sometimes fitted with fixed attachment members for holding the medical equipment or IV equipment so that the patient can be transported more easily. While these devices include poles for holding equipment, they are not suitable for use because the medical equipment or IV must be removed from the stationary pole of the patient's room to the fixed pole of the platform for mobility. In other words, the platform includes its own fixed pole that is different from the pole used by the patient, requiring moving equipment back and forth between the poles before and after transport. This process is typically performed by clinical staff (nurses, etc.), which wastes clinical effort of nurses and other staff unnecessarily. Furthermore, patient mobility is limited to the platform while in transport and storage of these devices is inefficient, as the fixed pole extends well beyond the dimensions of the transport platform.

In addition, some specially manufactured patient transport platforms have been developed that include permanently mounted folding clamps. While the folding nature of the clamp provides better storage solutions, these devices still have numerous limitations. First, because the attachment piece is integral to the transport platform, there is no way for patients using traditional transport platforms to retroactively attach the device to the existing platforms, Second, the device requires the patient (or a nurse or caregiver) to bend to the floor to open and close the foldable clamp, and the patient or caregiver must be capable of flipping a release mechanism to release the clamp. For patients with decreased capabilities due to age or effects of illness or medication, these physical requirements can be exhausting or even impossible.

What is needed is a device that allows for the mobile transport of patients with medical equipment or IV equipment that does not require tools or physical exertion to attach or operate the device, that is easy to operate, that can accommodate a range of IV pole types and diameters without configuration, that is easy to clean (repeatedly), that requires minimal maintenance, that is durable, safe to operate, and affordable to produce, and that allows patient transport platforms be stored easily while the device is attached to the platforms. These requirements are satisfied by the device of the present invention.

BRIEF OVERVIEW OF THE INVENTION

The present invention is directed to a device suitable for connecting n intravenous (IV) pole securely to the platform used in patient transport. This configuration can be applied to many different patient transport platforms which include but are not limited to gurneys, wheelchairs and wagons for children (in pediatric hospitals such wagons are used as a main platform of patient transport for children ages 18 months to 6 years). The primary benefit of the present invention, is that it provides assistance to patients, family members, caretakers/guardians, staff, and management regarding the efficient and safe transport of patients, especially those requiring transfusion of intravenous medications and other treatments that include and for allow mobile operation. In particular the present invention securely attaches and detaches an IV pole treatments, and/or other mobile medical equipment to a number of commonly used existing patient transport platforms. This allows for patient mobility while also allowing the patient to continue receiving appropriate medical treatment while on-the-go.

Furthermore, to facilitate the transition between the stationary position and mobile transport seamlessly, the present invention can be securely attached without requiring tools or hand tightening. This allows for use by patients who may have limited dexterity or strength due to illness or medications. Furthermore, the present invention provides a deployable mechanism that attaches to the patient transport platform that can be deployed for operation, but that can be reconfigured for storage while still attached to the patient transport platform. When the device is stored, a safety lock can be used to prevent accidental deployment of the device. In one embodiment, electronic components of the device collect anonymous digital data of its functions. Data collected may include but is not limited to (a) state changes of non-moving parts (degrees of articulation/position relative to gravity), (b) state changes of moving components, (c) battery state status, (d) electric power generated/discharged, (e) number of rotations, (f) wireless connectivity, (g) digital storage utilization, (h) interval time between events, (i) ongoing time, (j) light (visible and/or non-visible wavelengths), (k) distance travelled and relative physical location, (l) temperature via a temperature sensor, and (m) humidity via a humidity sensor. This anonymous data is collected and transmitted wirelessly to a database, which may be accessible, for example, by the operator, analysists, and hospital administrators. Additional information related to maintenance and operation of the device may be communicated wirelessly as well. In one embodiment, power to the device may be provided by batteries or the device may produce its own power to use the electronic components. These and other objects, features, and advantages of the present invention will become better understood from a consideration of the following detailed description of the preferred embodiments and appended claims in conjunction with the drawings as described following:

DETAILED DESCRIPTION OF THE INVENTION

Generally speaking, the present invention is directed to a mounting and grasping assembly or device that allows for the connection of a first mobile equipment to a second mobile equipment, thereby providing a totally mobile singular unit allowing for full mobility. In the preferred embodiment the present invention is directed to a device suitable for connecting an intravenous (IV) pole or other medical equipment securely to a patient transport platform, such that the patient transport platform and other medical equipment can move together simultaneously. This configuration can be applied to many different patient transport platforms which include but are not limited to gurneys, wheelchairs, and wagons for children (in, pediatric hospitals such wagons are used as a main platform of patient transport for children ages 18 months 6 years). Generally speaking, the device of the present invention includes a mounting assembly that affixes (perhaps removably) the device to the patient transport platform, an arm assembly that extends from the patient transport platform, and a clip assembly that grasps the medical equipment to be moved with the patient transport platform. A catch assembly, an enclosure assembly, and an electronics housing assembly are incorporated to further provide the functionality of the device, as described more below. The device is configured to be connected to a patient transport platform, and in turn, the device removably affixes other equipment (such as an IV pole or equipment case) to the patient transport platform so that the platform, equipment, and patient may all move together. Various embodiments of the invention are shown in FIGS. 1-16. As noted above, while the preferred embodiment is to be used in medical settings for connecting a patient transport platform and other medical equipment for movement as a singular unit, it is contemplated that the invention is not necessarily so limited and other uses may be suitable. Still, for purposes of describing the invention, the preferred embodiment for case with the medical setting is used.

Figure 1:
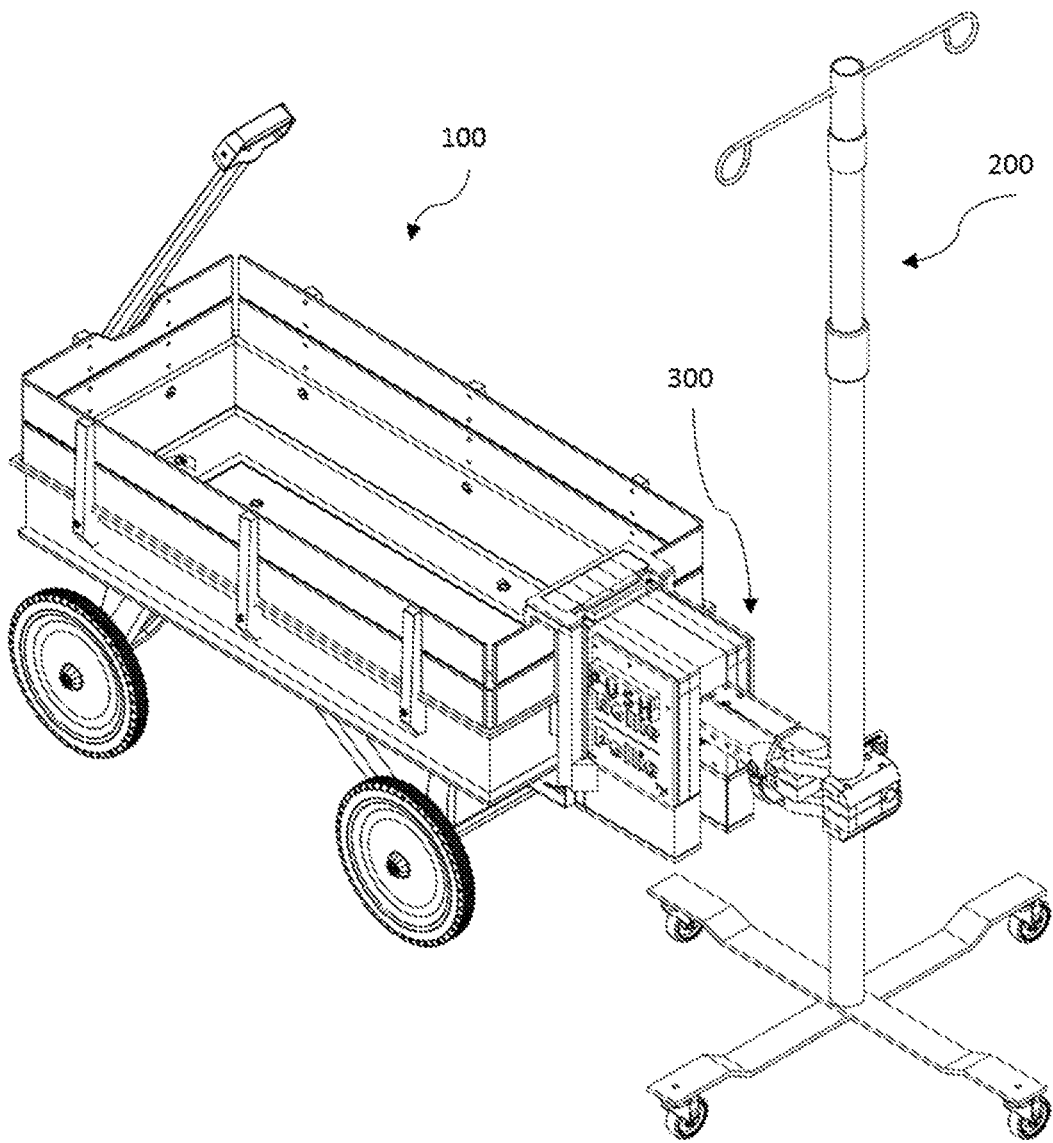
FIG. 1 is a perspective view of one embodiment of the present invention in typical operation, showing the device connecting a patient transport wagon and a mobile IV pole.
Figure 2:
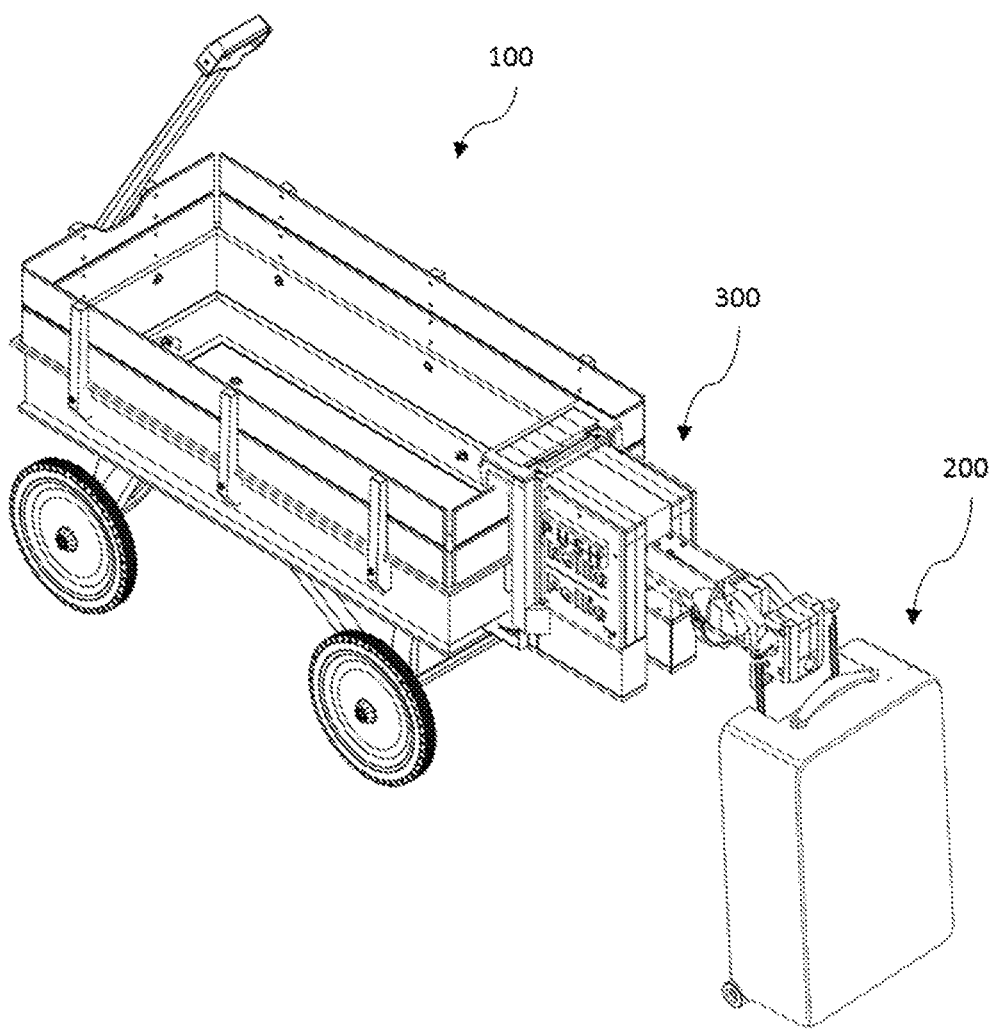
FIG. 2 is a perspective view of one embodiment of the present invention with rotated clip functionality, showing the device connecting a patient transport wagon and a mobile equipment storage case.

As noted above, the device 300 includes a number of components that work together to provide the full functionality contemplated—that is, the connection of the device 300 to the patient transport platform 100, the connection of the device 300 to the mobile equipment 200, and the use of the device 300 for storage of the patient transport platform 100, data collection and analysis associated with operation of the device 300 and patient transport platform 100, and other additional features. The connection of the device 300 to the patient transport platform 100 is achieved through a mounting assembly 305, which is described more fully below. As shown in FIGS. 1-2, the connection of the device 300 to the mobile equipment 200 to be moved with the patient transport platform 100 is achieved through a clip assembly 301, which is connected to the mounting assembly 305 (and other body components 303) through the arm assembly 302 (described more fully below). The clip assembly 301 is configured to securely mount the patient's IV pole or medical equipment 200 to the transport platform 100 through the device 300 of the present invention. In general terms, the clip assembly 301 is operable to open and close a dip around the medical equipment 200 to be moved, such as to grasp and release the medical equipment 200 as desired.

The clip assembly 301 includes a number of components, including a rotating connection piece 13 that connects the arm assembly 302 to the clip assembly 301. This junction 13 between the clip assembly 301 and arm assembly 302 rotates 90 degrees while maintaining a stable connection, allowing the mouth of the clip assembly 301 to be positioned in various directions so that different equipment 200 may be grasped for movement (compare, for example, FIG. 1 where the mouth of the clip assembly 301 is horizontally positioned, allowing for the grasping of an IV pole 200 to FIG. 2 where the mouth of the clip assembly 301 is vertically positioned, allowing for the grasping of a handle of a storage case 200). A bottom inner piece 14 and a top inner piece 15 of the clip assembly 301 connect to the rotating junction piece 13 and provide the physical structure of the clip body. A bottom outer piece 16 and a top outer piece 17 of the clip assembly 301 each attach to the corresponding bottom inner piece 14 and top inner piece 15 and provide additional support for the clip body. The bottom outer piece 16 and top outer piece 17 also house a self-adjusting feature of the clip assembly 301. An exploded view of one embodiment of the clip assembly is shown, for example, in FIG. 15. As shown the top outer piece 17 of the clip assembly 301 is curved to facilitate the transition of the device from the downward/kickstand position and upward/horizontal/active position. The top outer piece 17 allows the clip assembly and arm assembly to pivot the patient transport device from an inverted storage position to a horizontal position ready for use and movement. The curvature of the top outer piece 17 makes that transition much more fluid, and therefore requires less effort to deploy the device and attached patient transport platform from the kickstand position to the active position.

The assembled clip contains hidden and partially hidden components that function to center the IV pole, once it is the body of the clip. This self-centering positioning mechanism within the clip serves to provide appropriate contact with poles of various diameters. This feature uses specially designed "V" brackets 44, 45 that interface with the IV Pole or other equipment inserted into the mouth of the clip assembly 301. The second feature is a "V" shaped bracket that uses springs to press the bracket towards the center of the clip. The brackets adjust to the size of the item inserted into the clip, while also providing additional stability for items with a smaller diameter than the maximum accommodated by the clip. This feature was designed to better hold and center equipment that has smaller diameter than the dimension of the closed clip. This is especially useful for IV poles that have a smaller diameter than a standard pole. While the closed clip will secure even a smaller piece of equipment, the "V" shaped bracket within the clip will prevent the smaller pole from rattling in the clip as well as add a measure of security to the interface between the pole and the clip. The V brackets 44, 45 achieve this self-adjusting feature through the use of two expansion springs on each bracket, four in total. These springs allow the brackets to pivot into the space provided by parts the bottom outer piece 16 and top outer piece 17 of the clip assembly for larger objects, while providing maximum tension for smaller items inserted into the clip. The clip assembly also includes a release lever 18, 19. These parts 18, 19 connect to each other by three machine bolts/nuts and the unified configuration is contained by the body of the clip. The center connecting machine bolt is connected to a medium sized spring anchored inside of the clip body. This spring provides the necessary tension that keeps the clip in the closed position, while allowing easy transition between the open position or release position.

As noted previously, the device of the present invention includes an arm assembly 302, which is operable not only to connect the clip assembly 301 to the mounting assembly 304 (and other body components 303) to achieve the single-unit connectivity and mobility between the platform 100 and medical equipment 200, but also to provide functionality for storage and other means. For example, when the patient transport platform 100 is not in use, the device 300 is configured such that the arm assembly 302 is in the stored position, as shown for example in FIGS. 3-4, such that the arm assembly 302 acts as a kickstand for supporting the patient transport equipment 100. This allows for easy storage of the patient transport platform 100 even when the device 300 is attached to the platform 100. When ready for use, the arm assembly 302 of the device 300 is moved to the upright position, such that the device 300 can grasp some equipment 200 (using the clip assembly 301, described more fully above) and therefore provide a single transport-equipment unit for full mobility. To do this, the arm rotates outward through rotation of the spools of the arm assembly 302 to the upright position. This rotation outward to the upright position exposes the clip assembly 301, as shown in FIG. 1. As noted above, the clip assembly 301 may then be rotated according to use, and the clip assembly 301 is then opened to allow the IV pole (FIG. 1, for example) or medical equipment (FIG. 2, for example) to be mounted inside the clip assembly 301. As noted above, once the IV pole, or other equipment 200 is securely mounted inside the mouth the dip assembly 301 is released allowing the spring to cause the dip assembly 301 to firmly close around the IV pole, securing the pole in place. This allows for patient mobility while remaining connected to the vital fluids or medications being administered. It may be seen that while a clip assembly 301 is used to grasp the IV pole, the arm assembly 302 is configured to securely connect the clip assembly 301 to the mounting assembly 304 and other body components 303 (and therefore the patient transport platform 100 when the device 300 is affixed to the platform 100).

Figure 12:
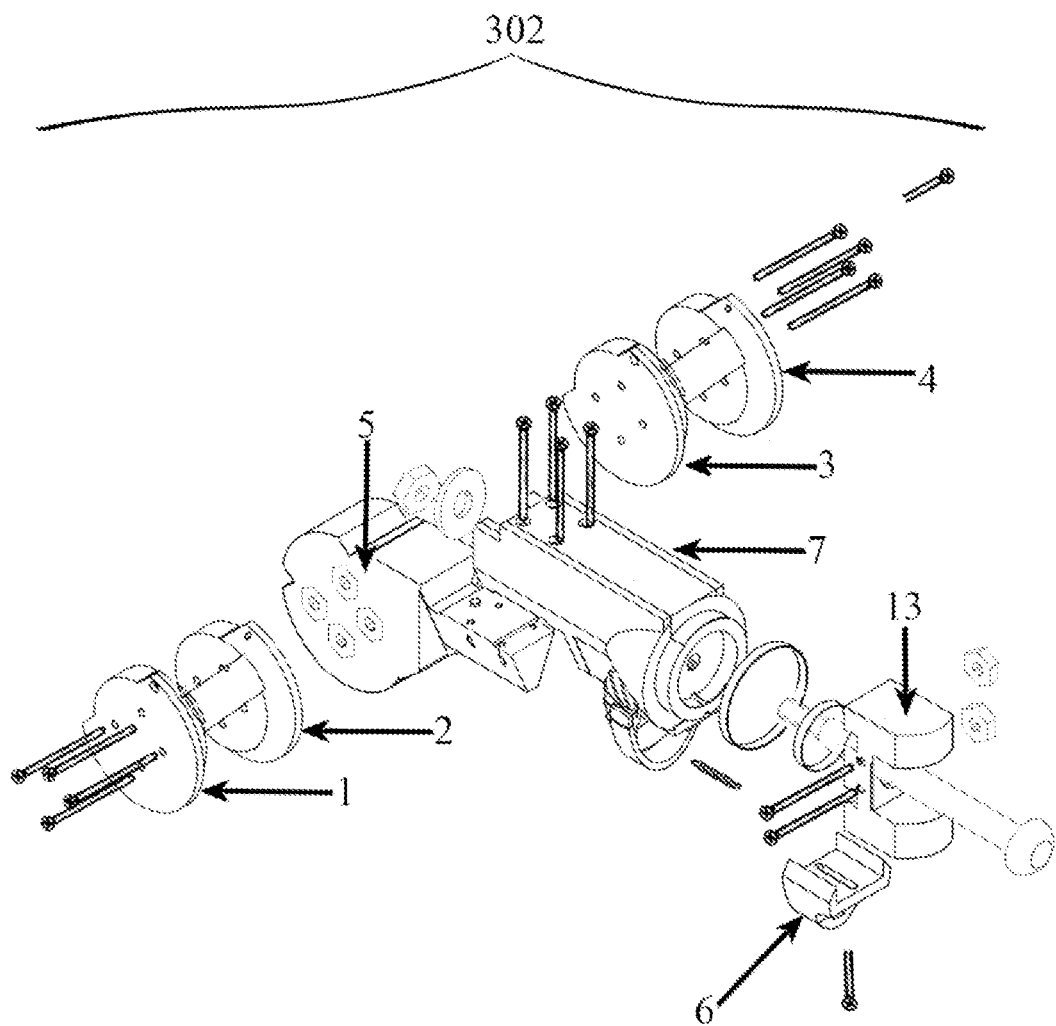
FIG. 12 is an exploded view showing one embodiment of the arm assembly of the device of the present invention.

An exploded view of one embodiment of the arm assembly is shown for example, in FIG. 12. The arm assembly 302 is preferably composed of nine components, four grooved interlocking spools 1, 2, 3, 4, one connecting piece 5, the arm housing 7, two slip rings for electric connection 46, 47, and a self-locking mechanism to se cure the connection between the arm and clip assemblies 6. Additionally, the assembly is preferably connected with four 3 mm machine bolts/nuts, one small mechanical spring, one 8 mm bolt/nut, and two 20 mm washers. The connecting piece 5 connects the spool of the arm assembly with the catch mechanism of the catch assembly (described below). The connecting piece 5 and the arm housing 7 have voids that allow space for electronic components that run throughout the device (described below). The unified configuration of the connecting piece 5 and arm housing 7 connect to the unified configurations of the interlocking spools 1, 2, 3, 4, as well as the self-locking mechanism 6. Arm assembly part 7, the arm housing, connects to the connection piece 5. The conduit of the arm housing provides a durable space for the electronic components supporting the sensors that are embedded in the arm and clip. The conduit also physically connects the clip to the arm through the use of a bolt/nut/washer junction.

Figure 3:
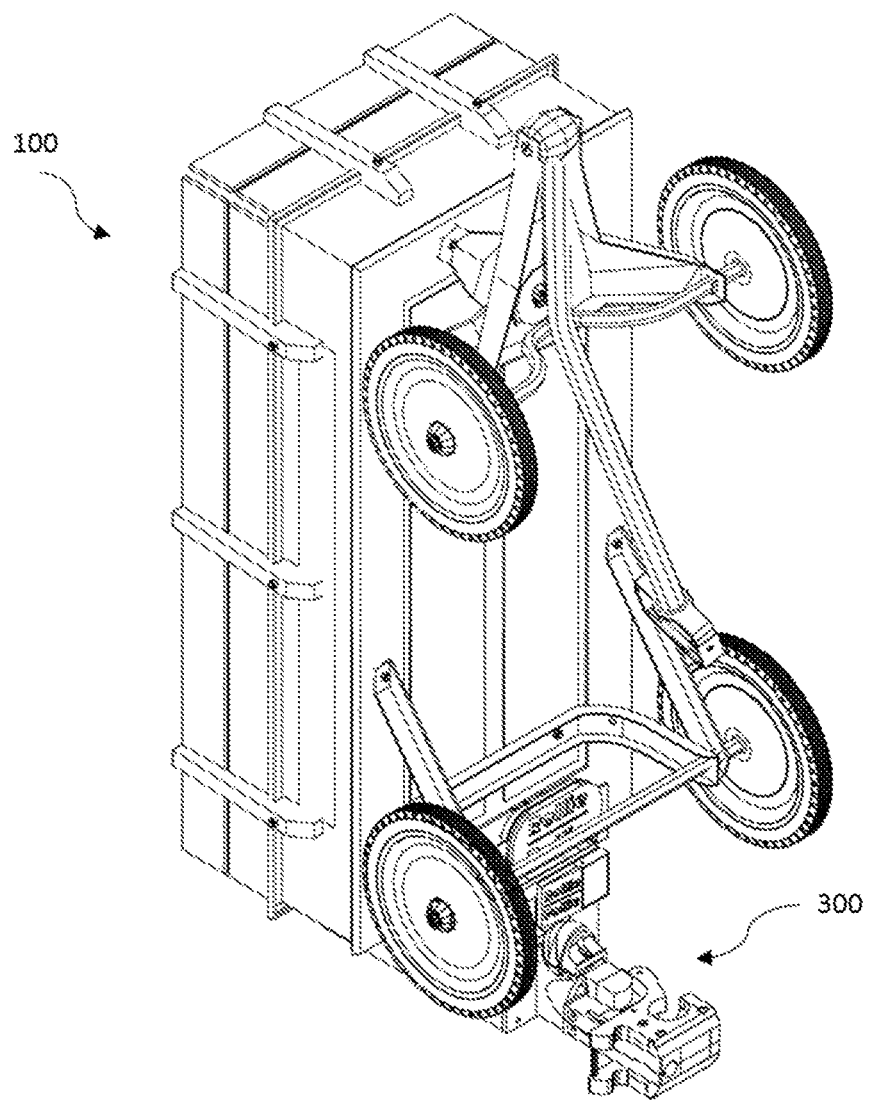
FIG. 3 is a perspective view showing one embodiment of the present invention, showing the kickstand functionality of the device.
Figure 4:
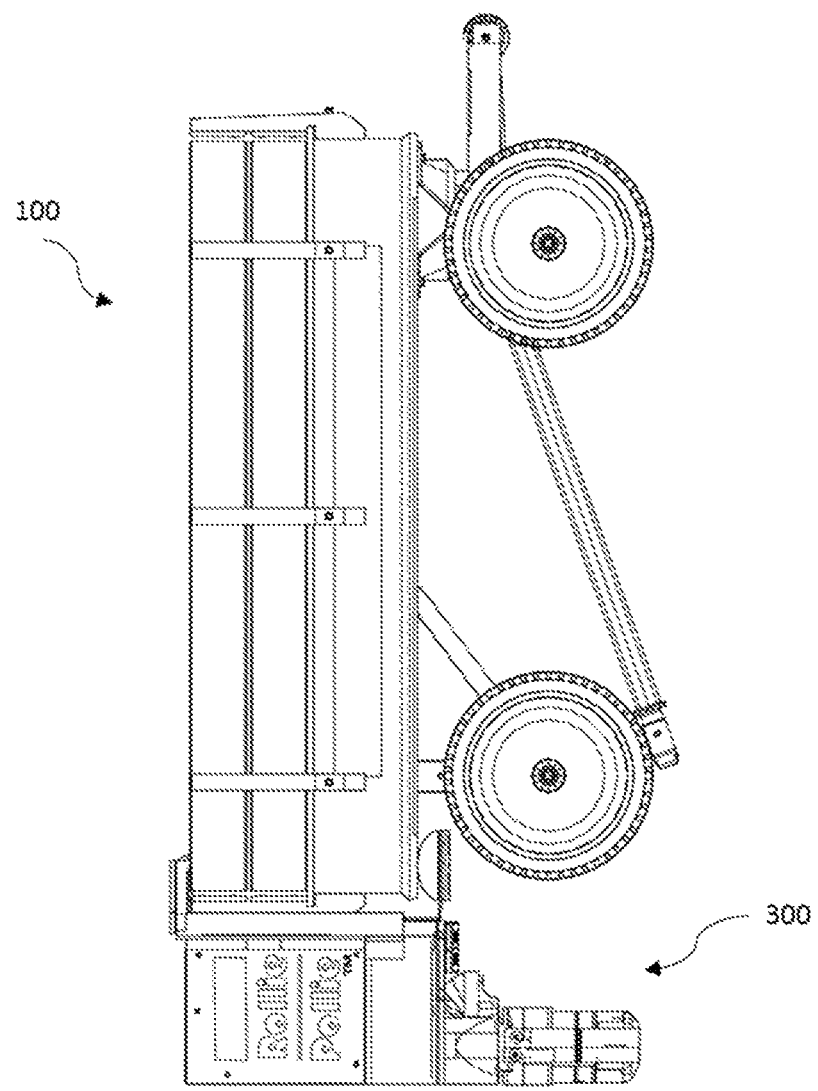
FIG. 4 is a side view showing one embodiment of the present invention, showing the kickstand functionality of the device.
Figure 5:
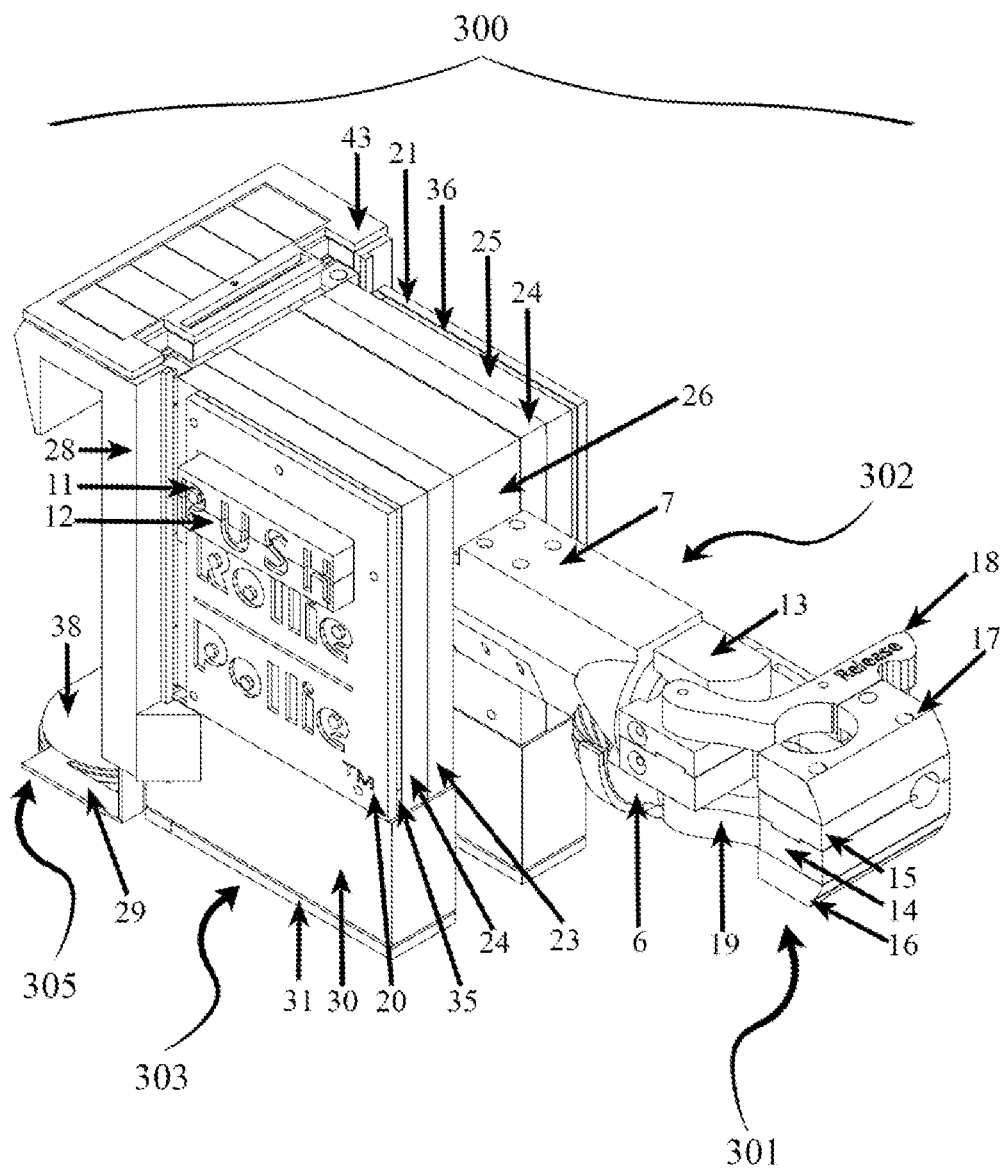
FIG. 5 is a front perspective view showing one embodiment of the device of the present invention.
Figure 6:
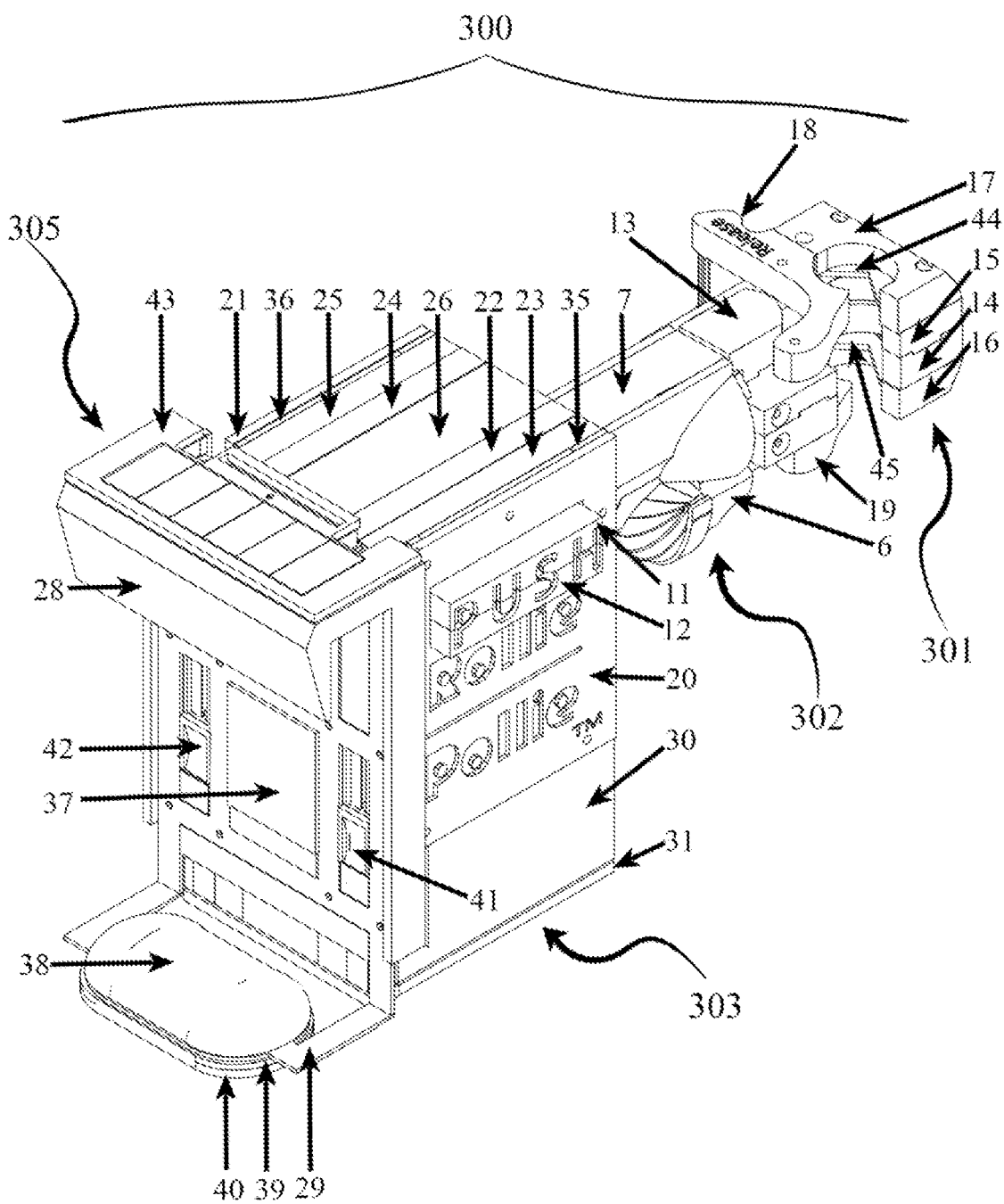
FIG. 6 is a rear perspective view showing one embodiment of the device of the present invention.
Figure 7:
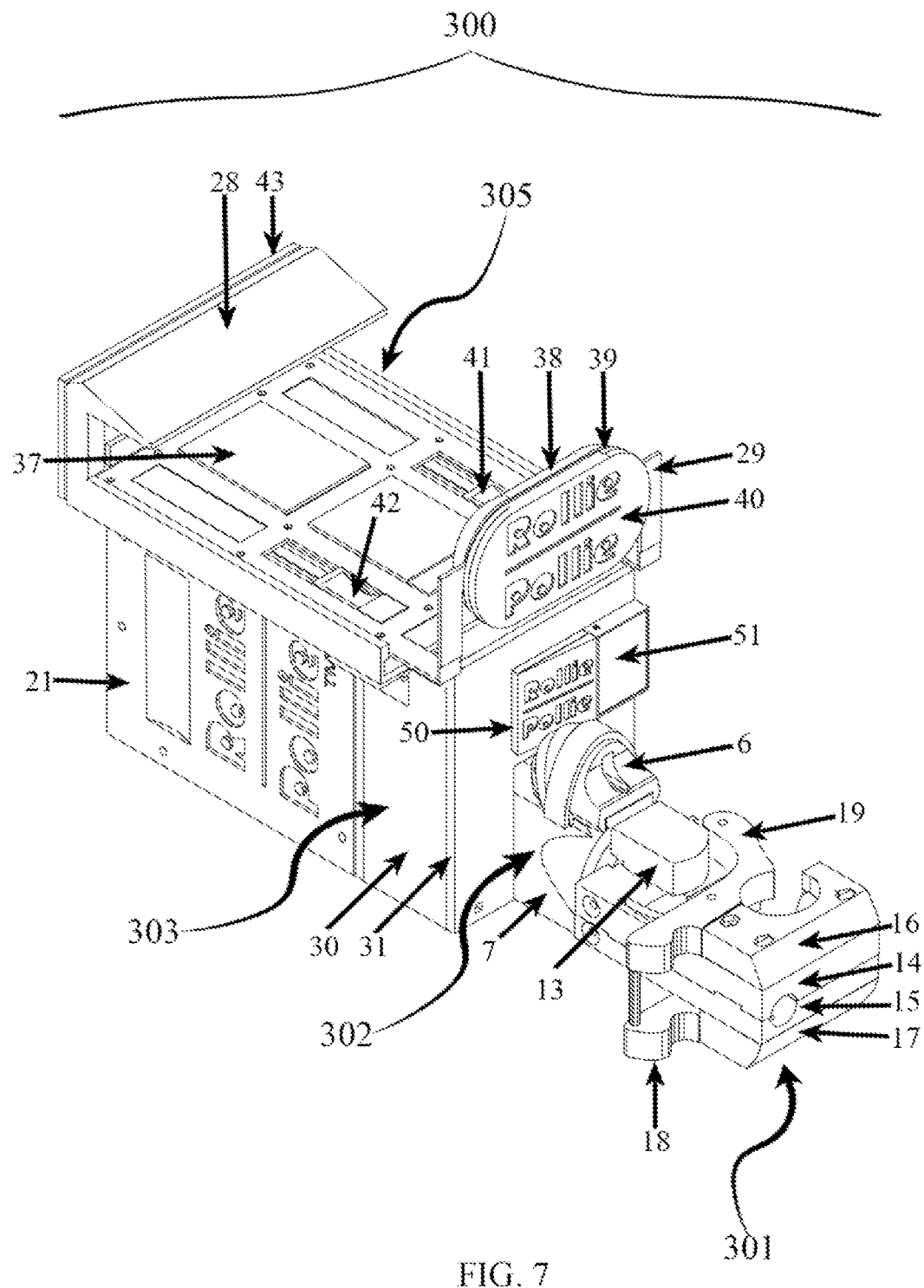
FIG. 7 is a front perspective view showing one embodiment of the device of the present invention in kickstand positioning and featuring a wireless charging module.
Figure 8:
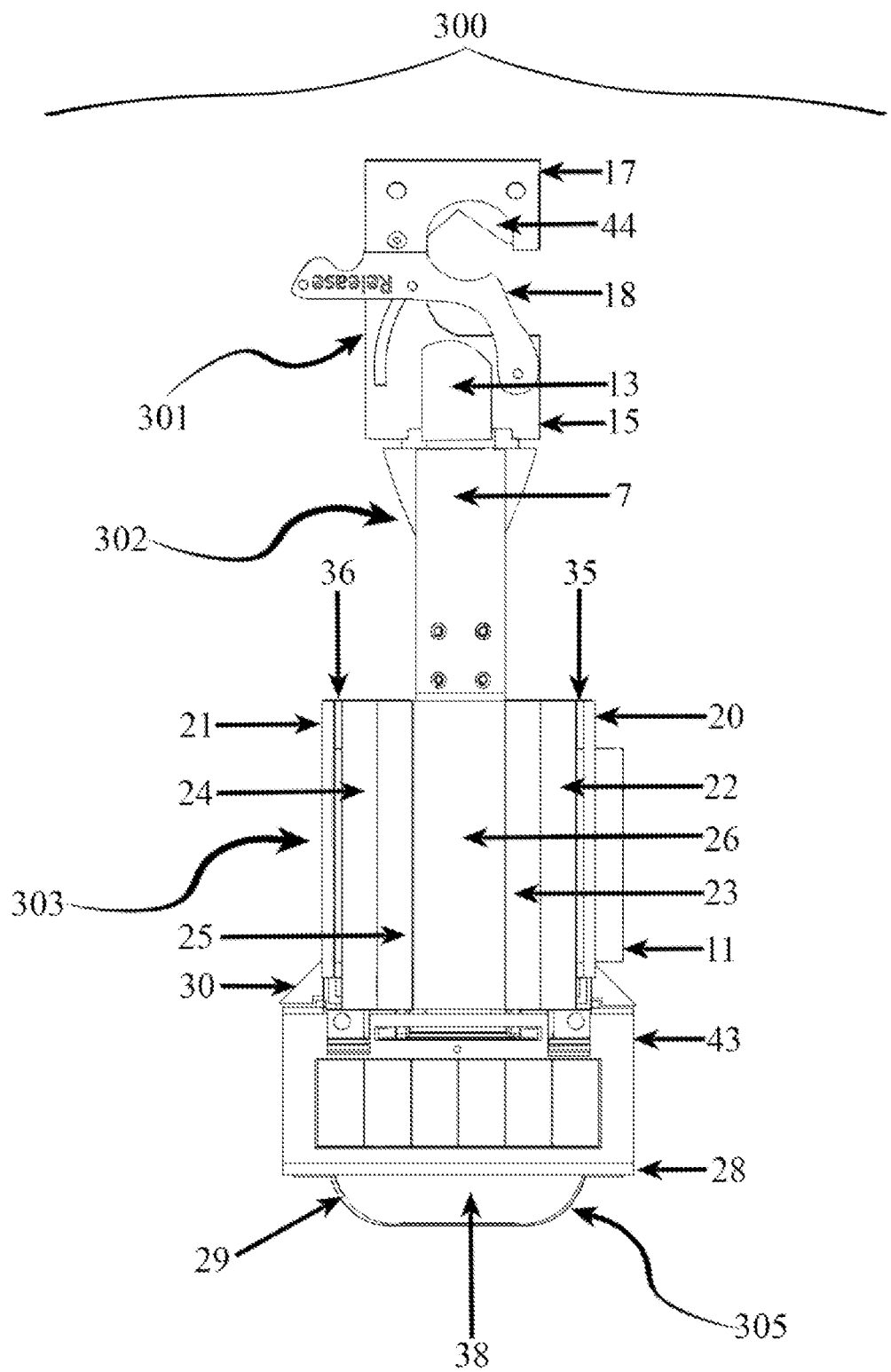
FIG. 8 is a top view showing one embodiment of the device of the present invention.
Figure 9:
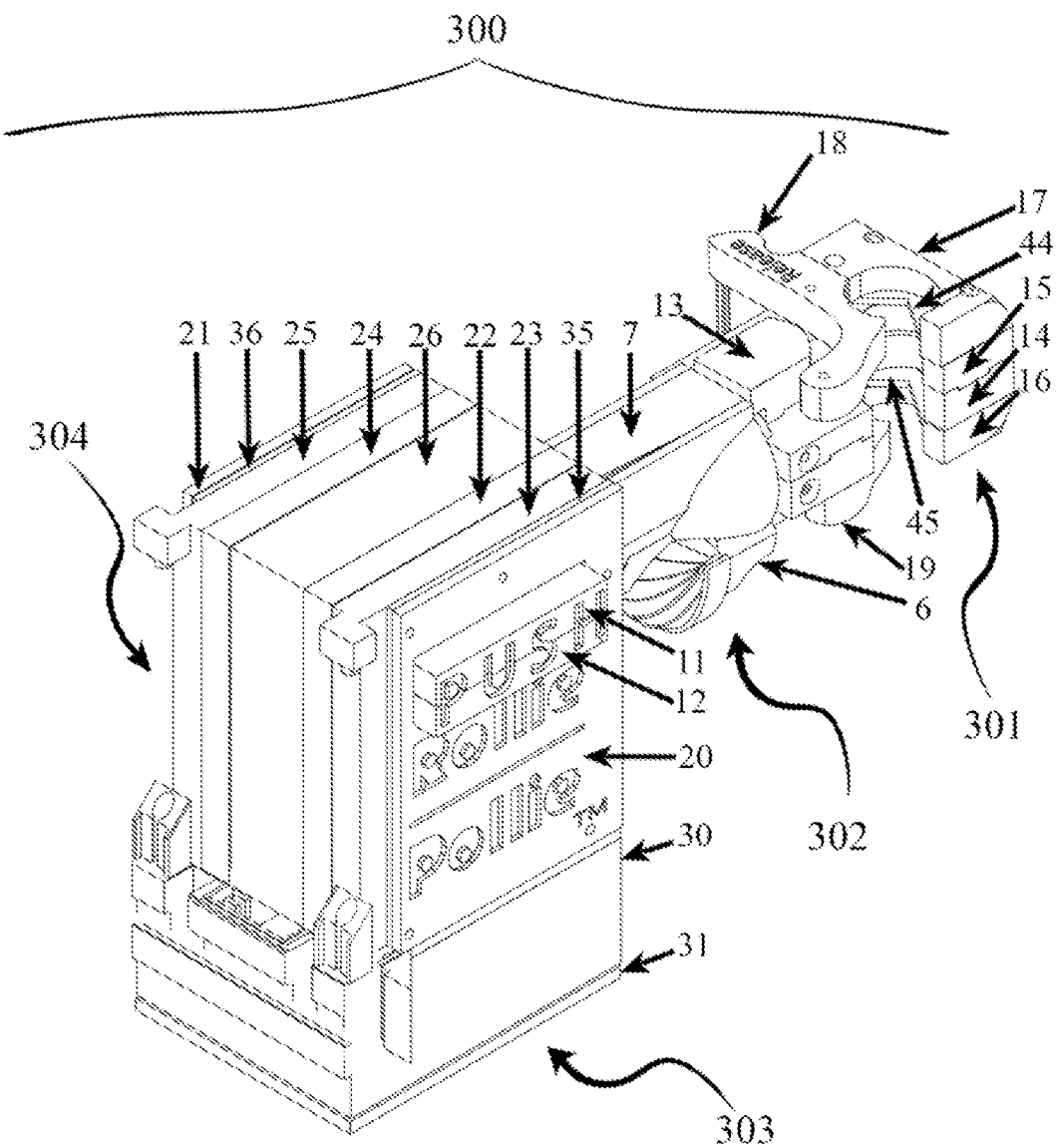
FIG. 9 is a rear per perspective view showing one embodiment of the device of the present invention.
Figure 10:
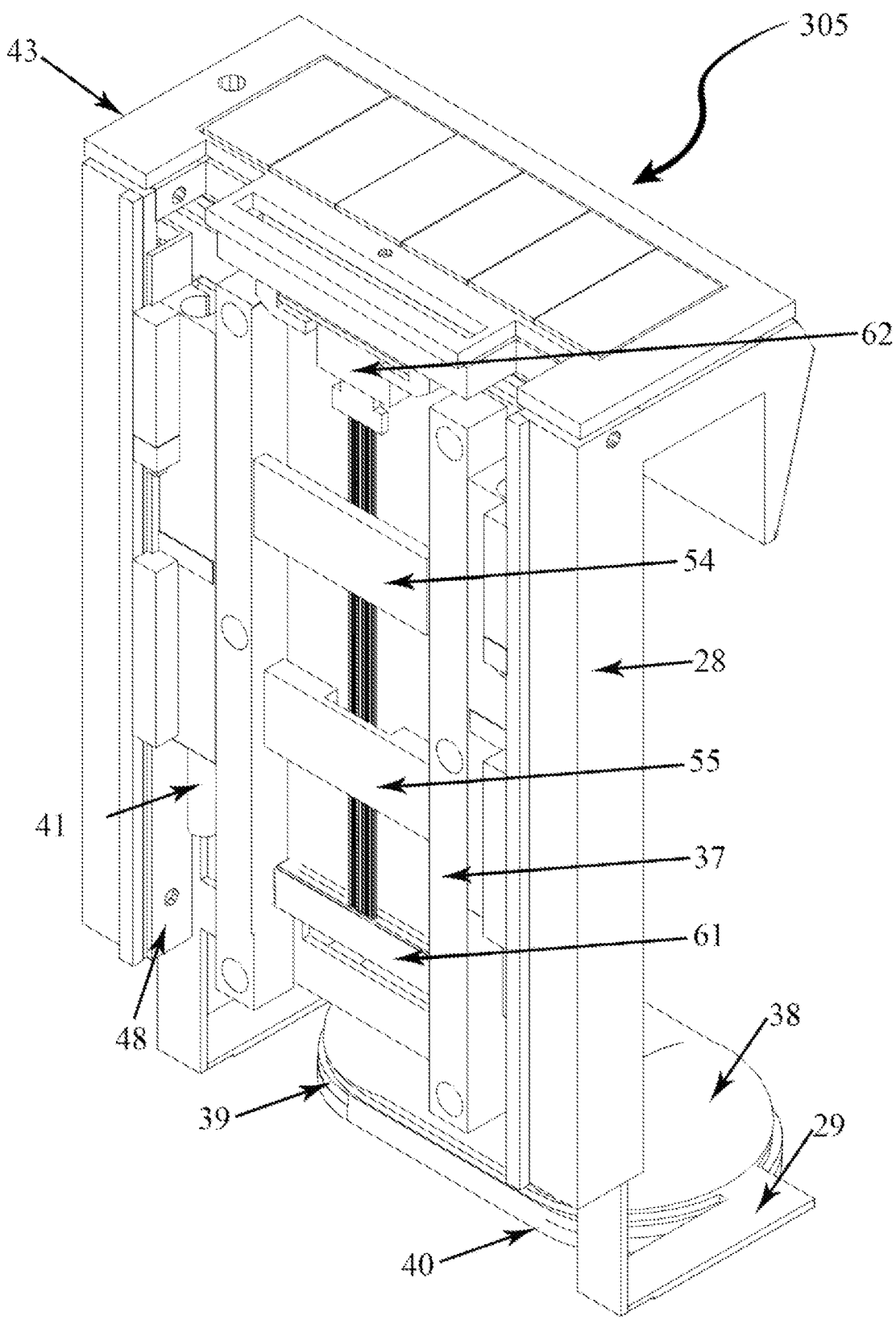
FIG. 10 is a perspective view showing one embodiment of the mounting assembly of the device of the present invention.
Figure 11:
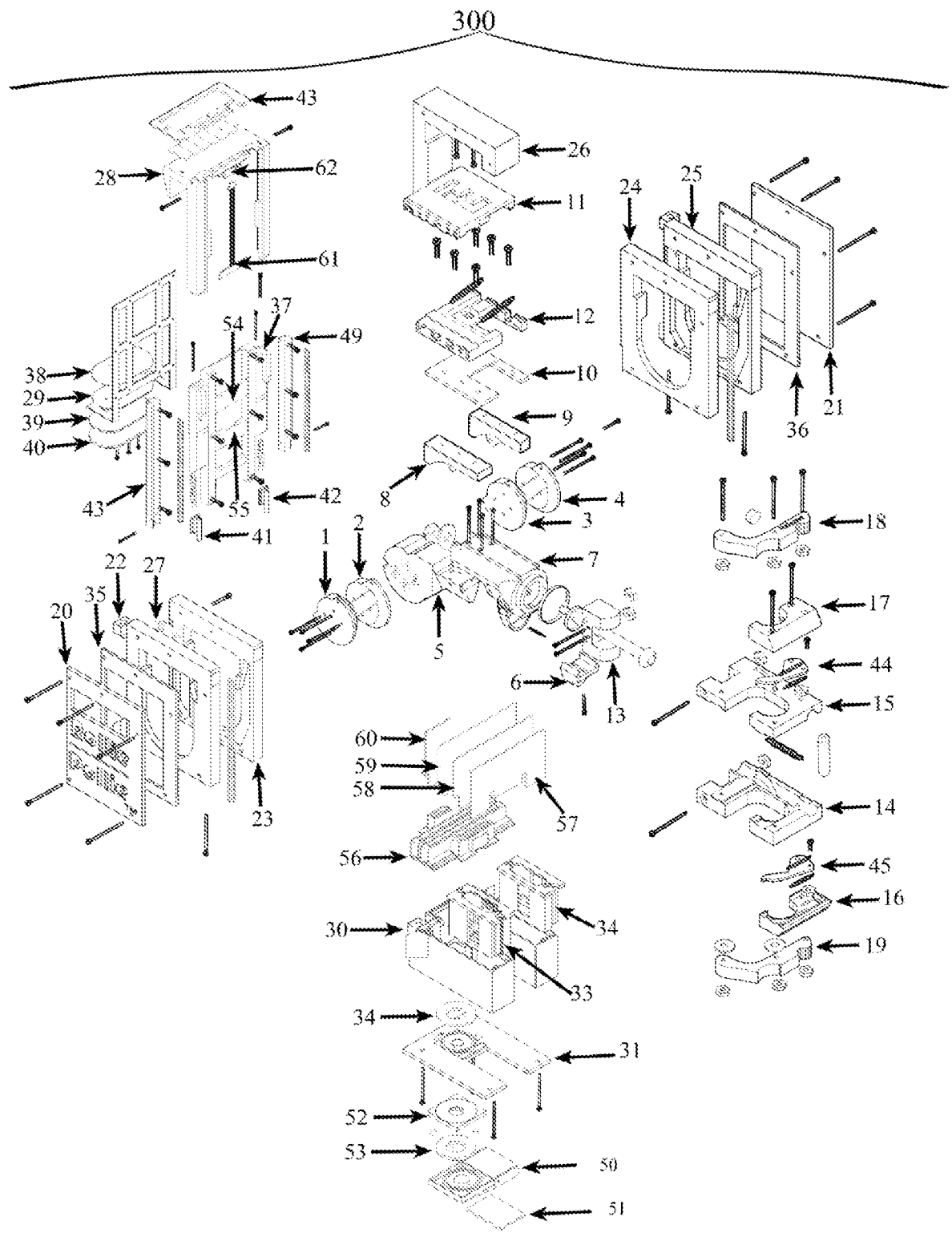
FIG. 11 is an exploded view showing one embodiment of the device of the present invention.

The catch assembly (an exploded view of one embodiment shown for example in FIG. 13) is configured to secure the arm of the device in either the upright or downward position (i.e. to allow for use of the arm assembly in movement of the platform or in storage of the platform, respectively) through a locking mechanism. The catch assembly includes five main parts: a left release component 8, a right release component 9, a center release component, 10, a top release component 11, and a release bottom component 12, all of which are secured to each other with six machine screws. The purpose of the top release component 11 and bottom release component 12 of the catch assembly is to provide the user access to the locking mechanism, that is they connect to form the "button" that emerges through the side window of the device's housing to allow the user to allow or prevent rotation of the arm assembly. The entire catch assembly is anchored to the rest of the device by two small springs connected to two additional machine screws. These springs and screws ensure that the assembly is returned to the locked position after the arm of the device has been rotated. A momentary contact switch on the interior of the device records that the "button" has been pressed, FIGS. 1-2, 5-6, 8, and 10 illustrate the configuration of the device once the "button" has been pressed and the catch assembly has been released and re-secured for the "up" position FIGS. 3-4 and 7 illustrate the "down" position.

Figure 13:
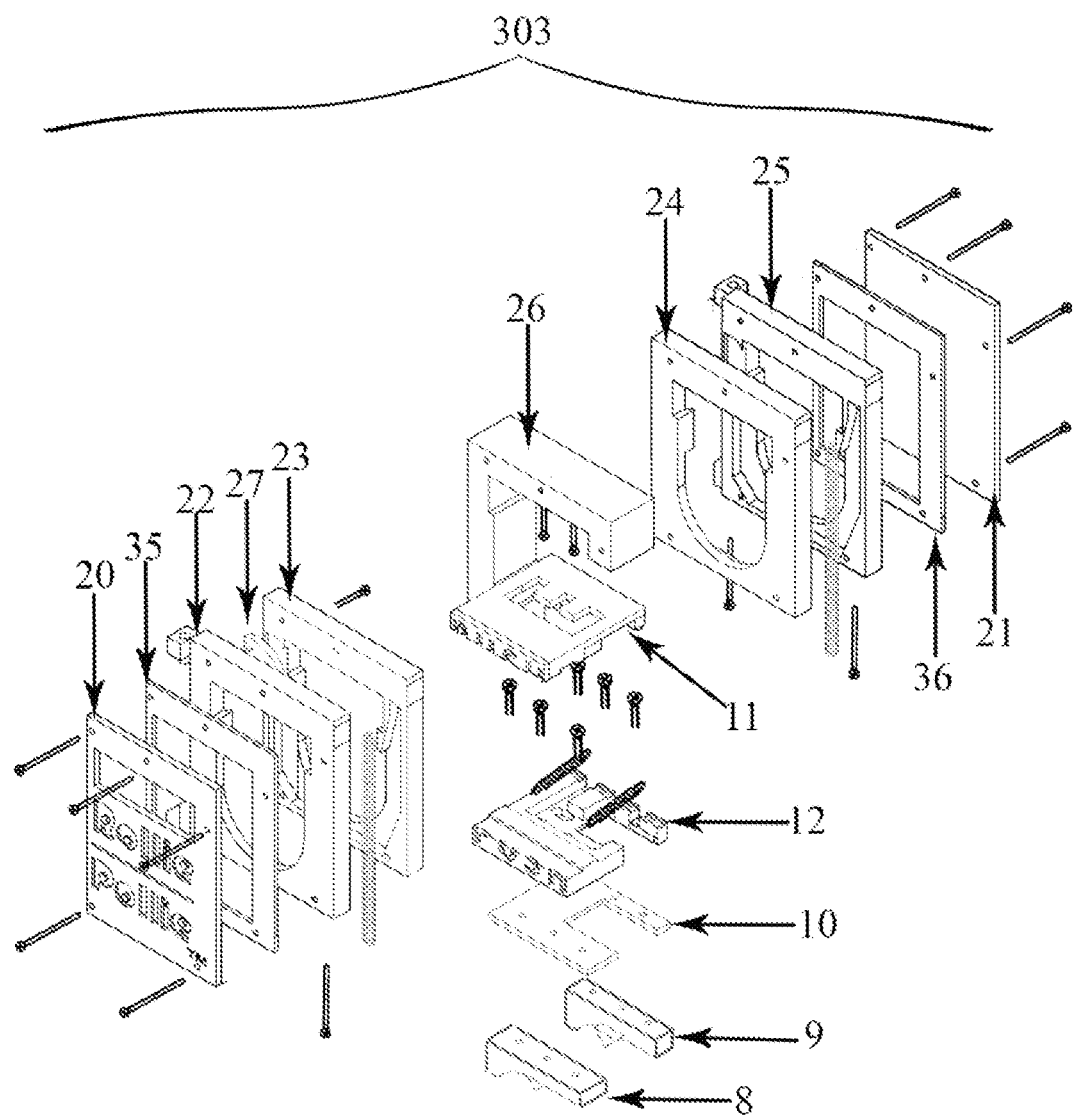
FIG. 13 is an exploded view showing one embodiment of the enclosure assembly of the present invention.
Figure 14:
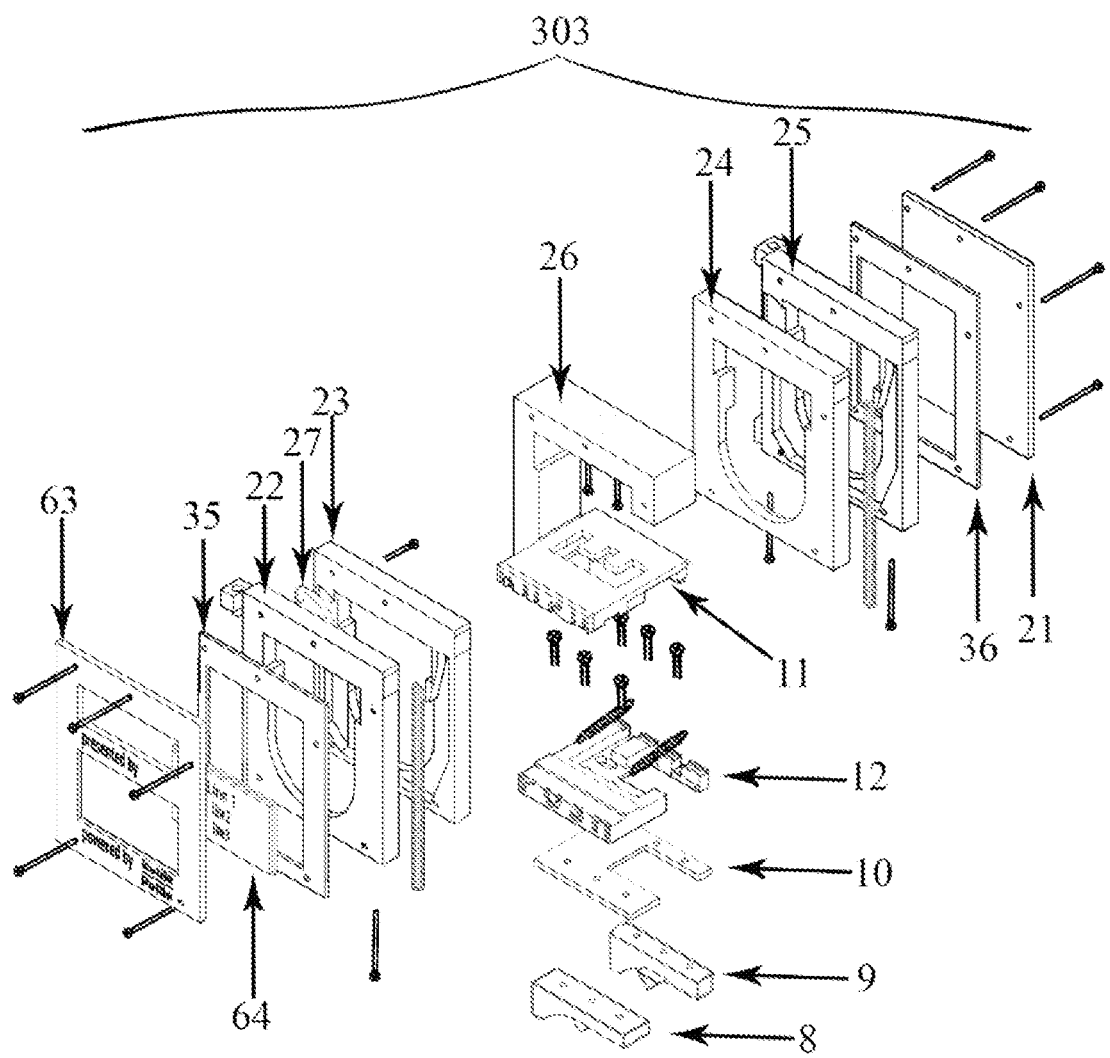
FIG. 14 is an exploded view showing one embodiment of alternate embodiment of the enclosure assembly of the present invention.
Figure 15:
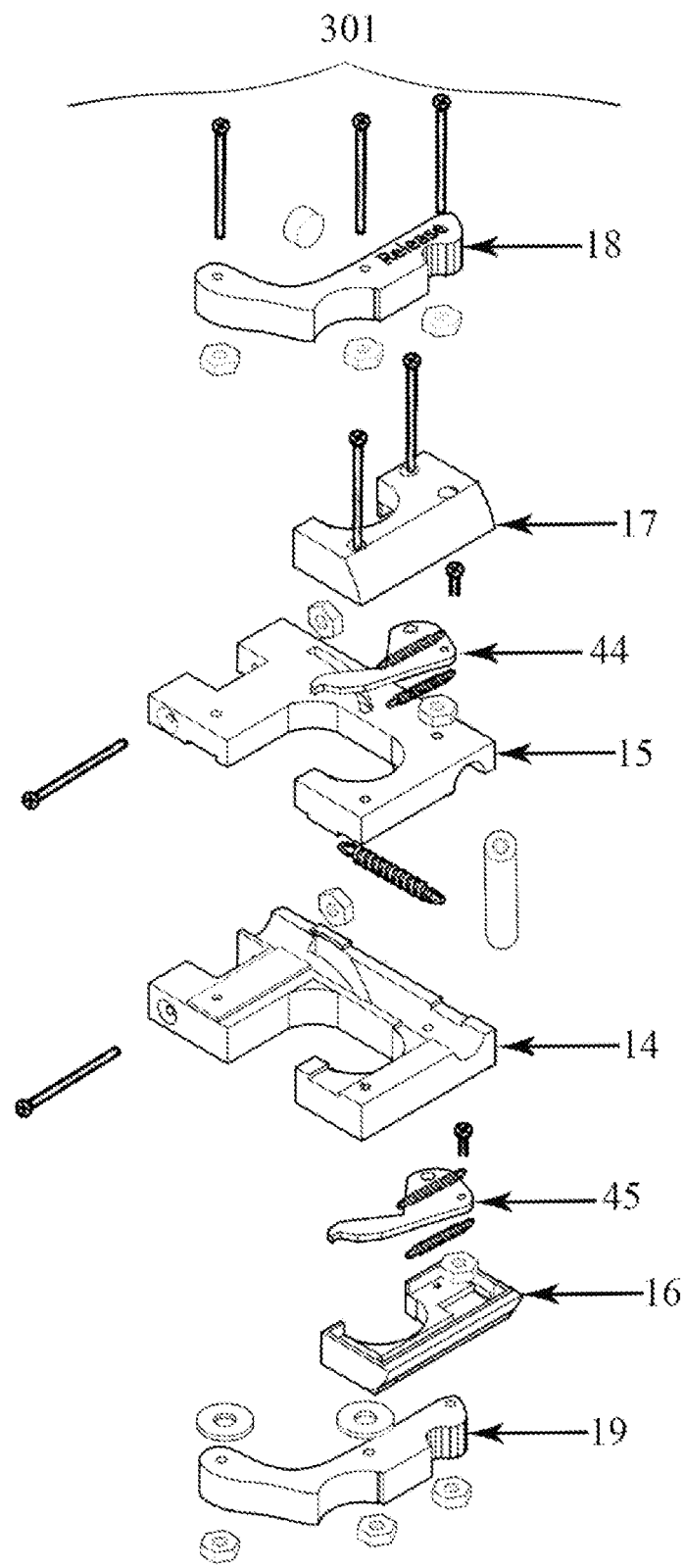
FIG. 15 is an exploded view showing one embodiment of the clip assembly of the present invention.
Figure 16:
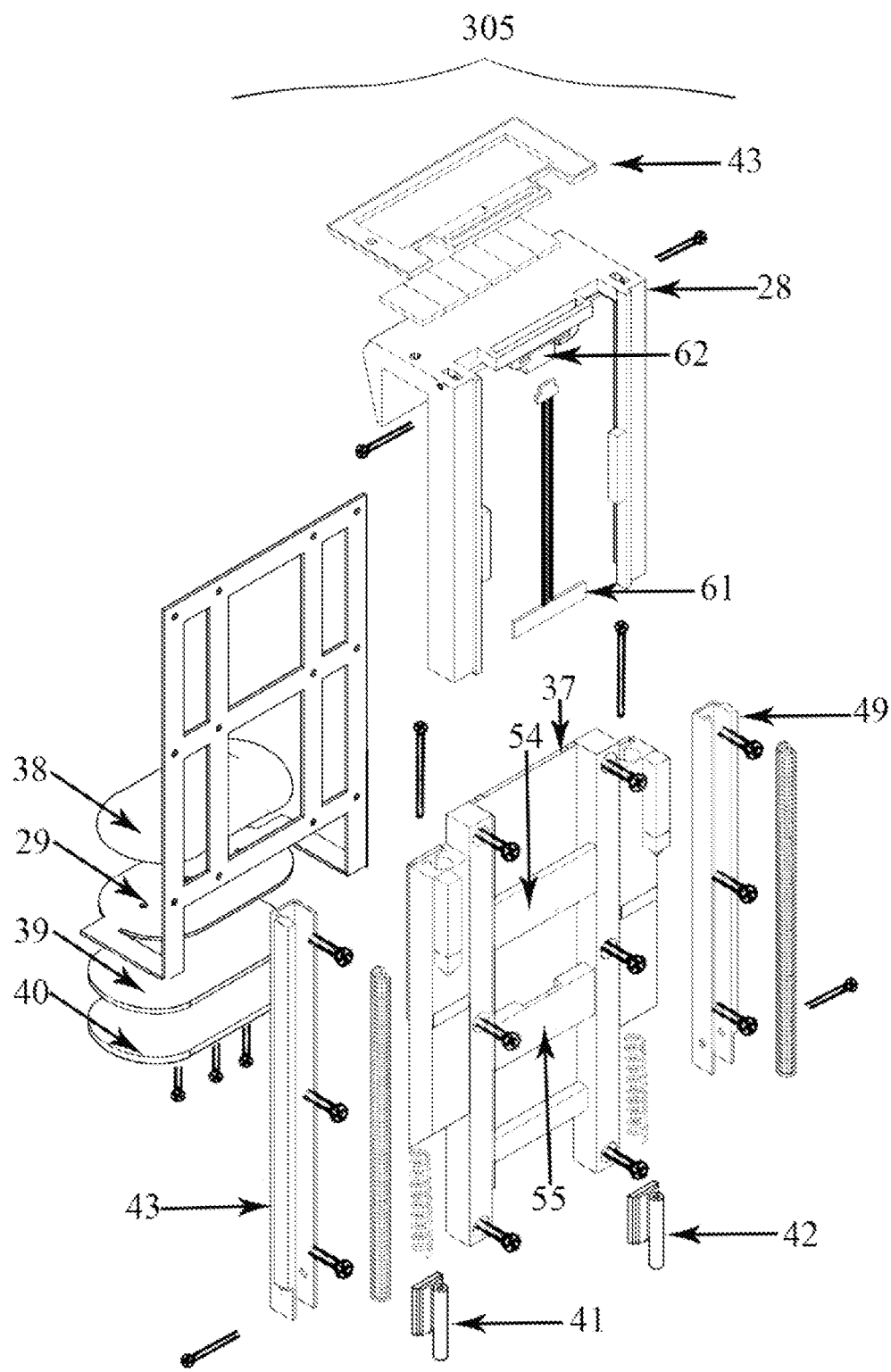
FIG. 16 is an exploded view showing one embodiment of the mounting assembly of the present invention.

In addition to the arm assembly, catch assembly, and clip assembly, the device of the present invention includes an enclosure assembly (various embodiments of which is shown in exploded views FIGS. 13 and 14). The interior enclosure for this device is composed of nine component parts: (a) two outer panels 20, 21, (b) two panel spacers 35, 36, (c) four interlocking spring housing enclosures, including a left outer spring housing 22, left inner spring housing 23, right inner spring housing 24, and right outer spring housing 25, and (c) one center support 26. Eight machine bolts connect the nine parts and two additional machine bolts/nuts connect the four corresponding parts 20, 35, 22, 23 on one side of the device and the other four corresponding parts 24, 25, 36, 21 on the other side of the device. The interlocking spring housing enclosures 22, 23, 24, 25 each provide structural support for the spring spindles 1, 2 of the arm assembly as support for the top release component 11 and bottom release component 12 of the catch assembly. The spring housing enclosures 22, 23, 24, 25 each also contain one of the two actuator extension springs that return the arm assembly from the stored "down" position to the active "up" position. Each of these springs attaches around the spools on each side and are anchored to the spring spindles 1, 2, 3, 4 of the assembly with short machine screws.

Additionally, the unified configuration of the spring housing 22, 23 contains the support for the safety mechanism 27, a medal pendulum that fits in a slot in the release top component 11 and release bottom component 12. This safety mechanism 27 has one degree of freedom within the enclosure between the spring house 22, 23. When the device is in "kickstand" mode, the tab protrudes from between the spring housing 22, 23 and rests in a notch in the release top component 11. This prevents the release top component 11 and release bottom component 12 from moving while the device is on the floor in the "kickstand" mode. This means that the device is prevented from accidently unlocking while in a vertical position and becoming unstable. The center support 26 of the enclosure assembly provides the structural support for most of the device. The center support 26 connects the return springs to the release top component 11 and release bottom component 12 as well. The enclosure assembly also includes panel spacers 35, 36 that are positioned between parts the cover plates 20, 21 and outer spring housings 22, 25 on either side of the enclosure assembly. These spacers 35, 36 prevent the sides of the spindles from rubbing against the interior of the cover plate 20, 21, which would create drag on the arm assembly. The additional width caused by the spacers 35, 36 also adds to the overall stability of the device while it's in the kickstand mode. In addition to the essential parts listed in the enclosure assembly there are two additional optional parts. The first is a cover plate 63 with a small rectangular void in the center of the panel. The second is a small rectangular panel 64 that fits the void of the optional cover plate 63. Together they completely cover the enclosure as the original cover plate 21 would, but the optional assembly 63, 64 would provide a means for special commemorations. Ideally, the small rectangular panel 64 would be personalized with the name(s) and/or other relevant information of the users, patients, etc. People are changed when they seek care from a hospital or other healthcare facility. This also allows a device to be dedicated in honor of a successful treatment or in celebration of the memory of a life lost.

The electronics housing assembly encloses the section of the device where electronics are housed. The electronics enclosure base 30 connects to the remaining components of the enclosure assembly through four bolts which are threaded directly into the parts of the housing listed above. The purpose of the base 30 is to provide additional stability of the device while attached to the patient transport platform when the patient transport platform is in the "Kickstand" mode for storage (i.e. placed in the down position), and to provide auxiliary enclosure space for additional electronic components. The electronical components of the device are integrated throughout the device, but most of those components are housed in the space provided in the base 30.

Generally speaking, the device is powered in two main ways, through solar and wireless charging. Direct charging to the power circuit board is also possible, but only in a maintenance situation as the base 30 must be removed from the rest of the device to access the correct circuit board. Since one of the goals of this device is to provide a means to access to the therapeutic benefits of natural light, a solar panel is integrated on top of the upper grip. This feature and its placement provide an ideal to use the natural light to power the device as well as make readings regarding the quality and, duration of the exposure to the light. A charging LED illuminates when there is sufficient light for the solar panel to produce electricity. Additionally, a wireless charging panel 31 is located on the bottom of the device underneath the electronics enclosure. This wireless charging panel 31 is a modular component that channels electricity from the wireless charging unit to the motherboard in the electronics enclosure. The charging panel 31 has the same 2-D profile of the electronics enclosure, and securely connects to the device using the same four bolts is as the electronics enclosure. This panel 31 contains a coil of wire that that is housed within a compartment in the panel 31. Four small but powerful magnets are embedded at the corners of the coil. A second coil is connected to an outside power source, a small enclosure houses the electronics to power the coil. Another set of four magnets align with those on the charging panel 31. The magnets attract in such a way that the enclosure transmitting power is held securely in the correct position to transfer power to the receiving coil. Another charging LED near the coil embedded in the wireless charging panel 31 illuminates when the receiving coil has enough power to charge the batteries of the device. A battery clip 2, 33 electrically connects to the wireless charging panel 31 and secures the receiving induction coil to the charging panel 31.

The small enclosure that transmits power to the wireless panel 31 also is equipped with an LED to indicated that the module is connected to a sufficient power source. Blocking diodes and smart charging circuits allow both the solar and wireless charging to be active without damaging the batteries or the connected electronics. The wireless charging panel 31 is designed to be modular. Bolts connecting the electronics enclosure to the rest of the device also connect the wireless charging panel 31. The wireless charging panel connects through a small slot in the bottom of the electronics enclosure, a male micro USB connector is wired to the receiving induction coil. The female micro USB connector inside the electronics enclosure transmits power directly to the charging circuits. The removeable module used to transfer power to the wireless charging panel is made of four parts: (a) a wireless charger enclosure 50, (b) a wireless charger cover panel 51, (c) a wireless charger coil enclosure 52, and (d) a wireless charger coil panel 53. The charger enclosure 50 houses the electronics that connect a micro USB DC power source to the transmitting power coil. A power LED on the side of the charger enclosure 50 indicates that electricity is coming into the circuits to be transmitted. The wireless charger cover panel 51 is a simple lid for the charger enclosure 50. The lid 51 is not designed to be routinely opened after the electronics have been placed inside the charger enclosure 50. After the lid 51 is pressed into place, an adhesive is used to secure it. The wireless charger coil enclosure 52 fits over the transmitting charging coil. The coil enclosure 52 also houses four small magnets arranged in a square around the coil. This provides correct positioning of the charger when placed in proximity to the bottom of the wireless charging plate 31. The wireless charger coil panel 53 is identical to the wireless charging coil cover 34. Since the transmitting and receiving coils are identical the panel that covers each of them also has the same function and dimensions.

Stacked inside the electronics closure 30 are (a) two battery clips 33, 34, (b) one motherboard 56, and (c) four circuit board modules 57, 58, 59, 60. The battery clips 33, 34 are designed to hold three 3.7v 18650 rechargeable batteries each, holding six batteries total. The terminal leads on the clips 33, 34 are side by side. In addition to the two functional leads near the bottom of the clips 33, 34 there are two additional testing leads on the top of each of the clips 33, 34. The test leads are for diagnostic evaluation rather than operational. Also, on the top of each of the clips 33, 34 is a large opening between the testing leads. This opening is to expedite removal of the batteries from the clip 33, 34 should they need to be changed. The modular design of each of the clips 33, 34 allows for the removal or insertion in a "hot-swappable" manner. In fact, the device can function with only one clip 33, should there be a need to remove the other clip 34 for diagnostic or maintenance tasks. The electronics motherboard 56 contains four PCI slots (30-pin (1), 72-pin (2), 12-pin (1)) and one micro USB receptacle. The purpose of this part is to connect power and data in such a way that supports the collection and dissemination of digital event logs. The motherboard 56 is designed to fit inside a reset space within the electronics enclosure 30. No tools are needed to install or remove the motherboard 56 or any of the parts that connect to it. Grooves on the electronics enclosure base 30 align with the slots on the motherboard 56 as an additional means of mechanical support for the various installed circuit boards.

The power circuit board 57 fits into the 30-pin slot on the motherboard 56. It connects directly to the batter clips 32, 33 via mounted terminal spring leads. The function of this circuit board 57 is to manage the correct flow of electricity. It receives incoming electricity from the solar and wireless charger and converts it to a suitable voltage for the charging batteries without damaging them. Additionally, it converts the electricity coming from the batteries to 3.3v (used by the microprocessor and sensor and 5v (used by the LED array primarily). Not all of the pins are used in the slot for electrical connection, however all of the contact with the connector used for mechanical support of the circuit board.

The sensor circuit board 58 fits into the first of the 72-pin slots on the motherboard 56. The function of this circuit board is to connect various sensors (Light Intensity (1 of 2), temperature (1), humidity (1), Hall effect (2), and accelerometers (2)) to power and facilitate the correct flow of data. Not all of the pins are used in the slot for electrical connection, however all of the contact with the connector is used for mechanical support of the circuit board. Special note: while the sensor circuits maybe located on this board relevant leads are housed throughout the device to accurately record various events. The first is a sensor that detects a range of light including those on the ultraviolet spectrum. A small opening in the casing allows for the sensor to detect the intensity of ambient light. Sensors recording temperature and humidity are included as other variables that may impact the use of the device and are therefore also included. Hall effect sensors located in the arm clip of the device are used with small magnets to detect state changes in the device that signal different events related to the operation of the device. Accelerometer is also used to detect orientation as well as acceleration. In addition to relying information, the wi-fi component also is used as means to determine relative indoor position using triangulation of the wi-fi signals. The micro-controller circuit board 59 fits in the second of the 72-pin slots on the motherboard 56. The function of this circuit board 59 is to connect the micro-controller (enabled with Wi-Fi and Bluetooth capability) to power and facilitate the correct flow of data. The wireless functions of the microcontroller are used to upload anonymous data for reporting, as well as determining placement and distance within a facility through the telemetry the available Internet access ports. Not all of the pins are used in the slot for electrical connection, however all of the contact with the connector is used for mechanical support of the circuit board. The rear panel interface circuit board 60 fits the 12-pin slot of the motherboard 56. The function of this circuit board 60 is to connect the electronics found in the rear assembly to the rest of the electronics in the device. Spring terminal leads are used to for the electrical interface with the rear assembly, as the removal of that assembly is rapid.

The final assembly is the platform/device mounting assembly; this collection of parts which connects the functional parts of the device securely to the platform. When the device is fully assembled, the device is mounted to the patient transport platform. This assembly allows that once it securely place it will snap into place it proves appropriate tension to securely attach the device to the platform. The mounting assembly includes a modular grip assembly, such that the rear section of the device is designed so that it can be easily and quickly removed from the patient transport platform. Numerous modules are designed to securely connect to a wider array of medical platforms. This assembly is designed in such a way to allow for a seamless attachment and removal of the device to the platform without the aid of tools or excessive effort.

The upper grip 28 of the mounting assembly provides the means to attach the device to a patent transport platform such that the device is mounted securely in place until it is removed. The upper grip 28 also provides a platform for the LED array, the solar panel, charging LED, and light sensor. The electronics housed in the electronics enclosure base 30 are connected to these items an upper grip electronics module 62 which is attached under the upper grip 28. The upper grip 28 is placed on the top of the assembly and is connected to top and bottom braces that are kept taught by two extension springs. The rear panel frame 29 is made of metal and provides a sturdy platform for the upper grip 28 and lower grip 38 as well as the interface that attaches to the device. The frame 29 is made of a single piece of steel for durability. The rear panel 37 connects directly to the real panel frame 29 and is anchored by six screws. On the right and left of the real panel 37 there are two channels that run the top to bottom. These channels have an embedded collar in the middle between the top and bottom. The outer spring housings 22, 25 connect to the top of the channel. A round peg the diameter of the channel fits tightly together. This configuration allows the outer spring housings 22, 25 to securely hang from the top of the rear panel 37. The bottom part of the panel 37 is truncated at an angle that matches the outer spring housings 22, 25. This angle allows for the quick separation of the entire rear assembly. The pegs at the top act as a point of pivot and latches 41, 42 keep the parts connected until they are pushed upwards away from the truncated joint. The lower grip 38 attaches directly to the metal back plate 29. The lower grip 38 is anchored by three screws and adhesive. The lower grip 38 is made of a rubber-like compound which provides a sufficient amount of contact necessary to remain securely connected to the patient vehicles when attached. The lower grip spacer 39 provides a necessary gap for the heads of the screws attaching the metal back plate 29 and lower grip 38, with the underside of the bottom grip. The spacer 39 is bonded to a lower grip cover 40. After the screws have been attached to the lower grip 38, the spacer 39 and cover 40 are bonded to the metal back plate 29 for a permanent placement.

The lower grip name plate 40 covers any potentially rough edges from the screws securing the grip to the frame or the frame itself. Additionally, the name plate provides important recognition while the device is in kickstand mode. The release tabs 41, 42 fit inside the right and left channels of a panel interface 37. A hole runs through each of the tabs 41, 42. A long-threaded machine screw is placed in the top of the panel interface 37 and pushed down into the channel until the collar in the middle prevents the head of the screw from going any deeper. Compression springs are placed in the opposite end followed by the release tabs 41, 42. The screw is tightened from above until the tabs 41, 42 are completely secured by the screws. This allows the tabs 41, 42 to move through the channel without falling out when they are released. An upper grip cover 43 is the top plate of the rear assembly. It provides a smooth finish, while also helping to secure the solar panel, LED array, and light sensor to the top of the upper grip 28. The grip spring guide 48, 49 are inside the two long structures on the right and left sides of the upper rip 28 are long springs. The spring guides attach to the rear panel frame 29 with 6 screws, three for each guide 48, 49. These guides 48, 49 house the remaining sides of the springs that connect the upper grip 28 and lower grip 38. The upper grip 28 anchors the tops of these springs while the lower grip 38 is anchored by the spring guides 48, 49. On the sides of these guides 48, 49 are raised tracks that match the grooves on the inside of the upper grip 28. These tracks and grooves ensure that the force from the springs is displaced in only one axis, up or down. The cable guide 54 (bottom) and 55 (top), are designed to keep the multichannel cable that connects the electronics on the top of the grip to those housed in part 30 from getting snagged during removal of the rear panel. The multi-channel flat cable 61 connects the upper grip electronics module 62 with the real panel circuit board 60. The end that connects to the circuit board 60 is mounted to the rear panel interface 37 with sturdy flat leads. The other end is directly inserted in to the 12-pin slot of the upper grip electronics module 62. Both ends of the cable are mounted on circuit board material for connectivity and durability. The cable is arranged so that when the upper grip 28 of the rear assembly moves the cable moves too without losing connection.

The upper grip electronics module 62 fits in an internal bracket formed by the upper grip 28. The module 62 connects the solar panel LED array, and light sensor to the other electronics of the device. A 12-pin slot is mounted to a small circuit board and mounted to the bracket of the upper grip 28. The various electronics on the upper grip 28 connect directly to the circuit board and 12-pin slot. Finally, the assembly also contains a self-limiting feature to prevent the top grip 28 from extending so far, the that the assembly separates when being attached to a patient platform. This is achieved by through an alignment of the upper grip 28 and the panel interface 37. Each of these parts has a block narrow block on each side that line up with the other. A gap between these blocks allows for the top and bottom grips to move away from each other only enough to attach or remove the device. When these blocks connect further movement apart is prohibited by the blocks making contact. This feature is further exploited as a momentary switch is in place at the end of the blocks on part 28. This allows data to be collected for the change in state when the rear panel is removed or installed.

Unless otherwise stated, all technical and scientific terms used herein have the same meaning a commonly understood by one of ordinary skill in the art to which this invention belongs. Although any methods and materials similar or equivalent to those described herein can also be used in the practice or testing of the present invention, a limited number of the exemplary methods and materials are described herein. It will be apparent to those skilled in the art that many more modifications are possible without departing from the inventive concepts herein.

All terms used herein should be interpreted in the broadest possible manner consistent with the context. In particular, the terms "comprise" and "comprising" should be interpreted as referring to elements, components, or steps in a non-exclusive manner indicating that the referenced elements, components, or steps may be present, or utilized, or combined with other elements, components, or steps that are not expressly referenced. When a Markush group or other grouping is used herein, all individual members of the group and all combinations and subcombinations possible of the group are intended to be individually included. All references cited herein are hereby incorporated by reference to the extent that there is no inconsistency with the disclosure of this specification. When a range is stated herein, the range is intended to include all sub-ranges within the range, as well as all individual points within the range. When "about," "approximately," or like terms are used herein, they are intended to include amounts, measurements, or the like that do not depart significantly from the expressly stated amount, measurement, or the like, such that the stated purpose of the apparatus or process is not lost.

The present invention has been described with reference to certain preferred and alternative embodiments that are intended to be exemplary only and not limiting to the full scope of the present invention, as set forth in the appended claims.

The invention claimed is:

1. A device useful for connecting mobile equipment to a mobile patient transport platform, thereby allowing simultaneous movement of the mobile equipment and patient transport platform, the device comprising:
   a. a device body comprising a mounting assembly operable to mount the device to the patient transport platform;
   b. a clip assembly comprising a mouth operable to grasp the mobile equipment, thereby securing the mobile equipment to the device;
   c. an arm assembly extending between the device body and the clip assembly, thereby operable to connect the patient transport platform and the mobile equipment through the device;
   wherein the clip assembly is connected to the arm assembly via a clip rotating connection piece, wherein the clip rotating connection piece is operable to selectively rotate the mouth of the clip assembly between a horizontal position and a vertical position; and
   wherein the arm assembly is connected to the device body via an arm rotating connection piece, wherein the arm rotating connection piece is operable to selectively rotate the arm assembly between an upward position and a downward position.

2. The device of claim 1, wherein the clip assembly further comprises a self-adjusting mechanism operable to variably adjust a diameter of the mouth to securely grasp mobile equipment of variable sizes.

3. The device of claim 1, wherein the arm assembly further comprises a number of spools operable to facilitate the rotation of the arm assembly.

4. The device of claim 1, further comprising a catch assembly comprising a locking mechanism operable to selectively lock the arm assembly in the selected one of the upward position and downward position.

5. The device of claim 4, wherein the catch assembly further comprises a button for selectively unlocking the locking mechanism to allow for rotation of the arm assembly.

6. The device of claim 1, wherein when the arm assembly is in the downward position, the arm assembly is operable to stabilize device for storage.

7. The device of claim 1, further comprising device electronics operable to at least one of (a) power the device and (b) collect data associated with operation of the device.

8. The device of claim 7, wherein the device electronics comprises at least one of (a) solar charging electronics operable to charge the device via solar power, (b) wireless charging electronics operable to wirelessly charge the device, (c) a light sensor, (d) a temperature sensor, (e) a humidity sensor, (f) a hall effect sensor, and (g) one or more accelerometers.

9. The device of claim 1, wherein the mobile equipment is an IV pole.

10. The device of claim 1, wherein the mobile equipment is an equipment case.

11. The device of claim 1, wherein the patient transport platform is one of (a) a wagon, (b) a wheelchair, and (c) a gurney.

12. A device useful for connecting mobile equipment to a mobile patient transport platform, thereby allowing simultaneous movement of the mobile equipment and patient transport platform, the device comprising:
  a. a device body operable to mount the device to the patient transport platform;
  b. a clip assembly comprising a mouth operable to grasp the mobile equipment, thereby securing the mobile equipment to the device;
  c. an arm assembly extending between the device body and the clip assembly, thereby operable to connect the patient transport platform and the mobile equipment through the device, wherein
    i. the clip assembly is connected to the arm assembly via a clip rotating connection piece, wherein the clip rotating connection piece is operable to selectively rotate the mouth of the clip assembly between a horizontal position and a vertical position; and
    ii. the arm assembly is connected to the device body via an arm rotating connection piece, wherein the arm rotating connection piece is operable to selectively rotate the arm assembly between an upward position and a downward position;
  d. a catch assembly comprising a locking mechanism operable selectively lock the arm assembly in the selected one of the upward position and downward position, wherein the catch assembly further comprises a button for selectively unlocking the locking mechanism thereby allowing rotation of the arm assembly; and
  e. device electronics operable to power the device and to collect operation data associated with the device, thereby allowing monitoring of the use of the device in movement of the patient transport platform and mobile equipment, wherein the device electronics, comprises at least one of (a) solar charging electronics operable to charge the device via solar power, (b) wireless charging electronics operable to wirelessly charge the device, (c) a light sensor, (d) a temperature sensor, (e) a humidity sensor, (f) a hall effect sensor, and (g) one or more accelerometers.

* * * * *